United States Patent [19]

Rogers

[11] 4,139,629
[45] Feb. 13, 1979

[54] PSEUDOMONIC ACID AMIDE ANTIBACTERIAL COMPOUNDS

[75] Inventor: Norman H. Rogers, Rudgwick, England

[73] Assignee: Beecham Group Limited, United Kingdom

[21] Appl. No.: 768,057

[22] Filed: Feb. 14, 1977

[30] Foreign Application Priority Data

Feb. 20, 1976 [GB] United Kingdom ................. 6884/76

[51] Int. Cl.$^2$ ..................... A61K 31/35; C07D 309/06
[52] U.S. Cl. .............................. 424/283; 260/345.8 R
[58] Field of Search .......... 260/345.7, 345.8, 345.8 R; 424/283

[56] References Cited

U.S. PATENT DOCUMENTS

| | | | |
|---|---|---|---|
| 3,483,227 | 12/1969 | Cragoe, Jr. et al. | 260/345.7 |
| 3,740,437 | 6/1973 | Harrison et al. | 260/345.7 |
| 3,755,603 | 8/1973 | Harrison et al. | 260/345.7 |

FOREIGN PATENT DOCUMENTS

1395907  5/1975  United Kingdom .................. 260/345.8

*Primary Examiner*—Nicky Chan
*Attorney, Agent, or Firm*—Jacobs & Jacobs

[57] ABSTRACT

Antibacterial compounds, preparation thereof, human and veterinary compositions containing the same and method of administration of the compositions without producing penicillinase and being amides of pseudomonic acid. The pseudomonic acid amides are effective against Gram-positive and Gram-negative organisms and possess good antimycoplasmal activity.

7 Claims, No Drawings

PSEUDOMONIC ACID AMIDE ANTIBACTERIAL COMPOUNDS

This invention relates to antibacterial compounds and in particular to a class of amides which have antibacterial activity against certain Gram-positive and Gram-negative organisms, in particular *Haemophilis influenzae* and *Neisseria gonorrhoeae;* and also possess good antimycoplasmal activity. The compounds are therefore of value in the treatment of veterinarybacterial infections and of particular value in humans in the treatment of bronchitis and venereal disease.

The routine treatment for gonorrhoeae has for many years been the use of penicillin antibiotics. However, some strains of gonococci are less sensitive to penicillins and the degree of such resistance has gradually increased resulting in larger doses of pencillins being required. Furthermore, there have been reports of strains which produce penicillinase, and are thus highly resistant to penicillin therapy. The British Medical Journal (1976) at page 963 comments: "Now the outlook for the control of gonorrhoeae has been radically changed for the worse by the portentous announcement of the existence of frankly resistant strains owing their resistance to the production of penicillinase, the penicillin-destroying enzyme found by many other bacterial species. This is a wholly new development, the consequences of which might well be disastrous."

We have now found that a class of compounds have high activities against many organisms including *N.gonorrhoeae*, and as the compounds are completely unrelated to the $\beta$-lactam type of antibiotics (including penicillins and cephalosporins), they are completely unaffected by penicillinase.

Pseudomonic acid is the E-isomer of the structure (I):

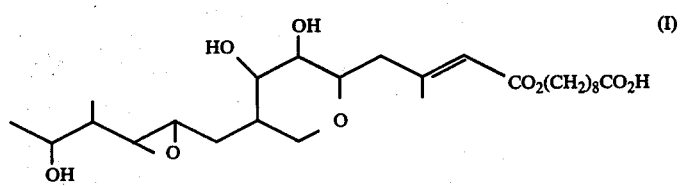

and is disclosed as having antibacterial activity in British Pat. No. 1,395,907. It has now been found that certain amides of pseudomonic acid have a lower serum binding than the acid itself, and are more active against certain organisms, in particular *Neisseria gonorrhoeae.*

Accordingly, the present invention provides a carboxylic acid amide of formula (II):

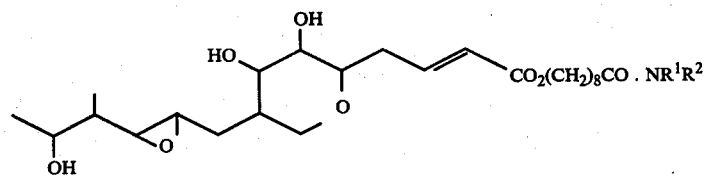

wherein $R^1$ and $R^2$ are the same or different and each represents hydrogen or an alkyl group.

Suitable alkyl groups for the groups $R^1$ and $R^2$ include $C_{1-6}$ alkyl groups such as methyl, ethyl, n-, and iso-propyl, n-, iso-, and tertbutyl.

Particular amide groups —$CO.NR^1R^2$ include the unsubstituted amide (—$CONH_2$), the N-methylamide, N,N-dimethylamide, and N,N-diethylamide.

The compounds of formula (II) may be prepared from pseudomonic acid of formula (I) by conventional techniques for producing amides of carboxylic acids.

Suitably a reactive derivative of pseudomonic acid is reacted with an amine $R^1R^2.NH$. Preferred reactive derivatives include mixed anhydrides formed for example with isobutylchloroformate, ethyl chloroformate, pivaloyl chloride and other reagents for generating mixed anhydrides. Alternative N-acylating derivatives of the acid (I) are activated esters such as esters with cyanomethanol, p-nitrophenol, 2,4-dinitrophenol, thiophenol, halophenol, including pentachlorophenol, monomethoxyphenol or 8-hydroxyquinoline; or amides such as N-acylsaccharins or N-acylphthalimides; or an alkylidene iminoester prepared by reaction of the acid (I) with an oxime.

Some activated esters, for example the ester formed with 1-hydroxybenztriazole or N-hydroxysuccinimide, may be prepared in situ by the reaction of the acid with the appropriate hydroxy compound in the presence of a carbodiimide, preferably dicyclohexylcarbodiimide.

Other reactive derivatives of pseudomonic acid include the reactive intermediate formed by reaction in situ with a condensing agent such as a carbodiimide, for example N,N-diethyl, dipropyl- or diisopropylcarbodiimide, N,N'-di-cyclohexylcarbodiimide, or N-ethyl-N'-$\gamma$-dimethyl aminopropylcarbodiimide; a suitable carbonyl compound, for example N,N'-carbonyldiimidazole or N,N'-carbonylditriazole.

Suitable solvents for the process of this invention include inert aprotic solvents, such as tetrahydrofuran, methylene dichloride, N,N-dimethylacetamide. The reaction is generally carried out at low temperature for example $-25°$ C. to $0°$ C., preferably at about $-10°$ C.

The antibiotic compounds according to the invention may be formulated for administration in any convenient way for use in human or veterinary medicine, by analogy with other antibiotics, and the invention therefore includes within its scope a pharmaceutical composition comprising a compound of formula (II) above together with a pharmaceutical carrier or excipient.

The compositions may be formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup methyl cellulose, glucose syrup, gelatin, hydroxyethylcellulose, carboxymethyl cellulose, aluminum stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository bases, e.g., cocoa, butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration. Where the compositions comprise dosage units, each unit will preferably contain from 50-500 mg. of the active ingredient. The dosage as employed for adult human treatment will preferably range from 100 to 3000 mg. per day, for instance 1500 mg. per day, depending on the route and frequency of administration.

The following Examples illustrate the present invention.

EXAMPLE 1

Pseudomonic acid N-methylamide

Sodium pseudomonoate (522 mg; 1mM) was dissolved in dry, distilled chloroformate (0.13ml; p = 1.04; 1mM) was added and the solution was maintained at $-10°$ C. for 10 minutes. A 1% w/v solution of methylamine in water (3.1 ml; 1mM) was added quickly and the solution was stirred for 1 hour with the temperature gradually warming to room temperature. The mixture was poured into water (ca 50 ml), saturated with sodium chloride and extracted with ethyl acetate (4 × 20 ml). The ethyl acetate extract was washed with saturated brine, dried over magnesium sulphate, filtered and the filtrate was evaporated to dryness in vacuo. (304 mg). Thin layer chromatography in chloroform/methanol 9:1 showed one major spot Rf = 0.3 with a trace of pseudomonic acid Rf = 0.21 and very small traces at Rf 0.40 and 0.47. This material was chromatographed on a 2 mm. thick silica HF 254 20 × 20 cm plate and eluted with 15% methanol in chloroform. The band at Rf = 0.35 (under U.V.) was removed and eluted from the silica with 20% methanol in chloroform. The resulting oily product was dissolved in ethyl acetate and washed thoroughly with aqueous sodium bicarbonate. The organic layer was dried over magnesium sulphate, filtered and evaporated in vacuo to give the product as an oil (127 mg).

Thin layer chromatography revealed 1 component Rf = 0.33 in chloroform/methanol 9:1 $_H$(CDCl$_3$) 0.92 (3H,d,12-Me), 1.20 (3H,d,13-Me), 9.30 (methylene envelope); 2.18 (3H,s, vinylic CH$_3$), 2.70 (m, epoxide protons), 2.76 (3H,d,N-Me), 5.75 (1H, broad s, vinylic H), 6.23 (—NH—); C (CDCl$_3$) 174.20 (1'-C,s,), 166.95 (1-C,s), 156.95 (1-C,s), 156-97 (3-C,s,), 117.71 (2-C,d), 75.07 (5-C,d), 71.47 (13-C,d), 70.60 (7-C,d), 69.11 (6-C,d), 65.43 (16-C,t), 63.83 (9'-C,t), 61.38 (11-C,d), 55.710 (10-C,d), 42.94 (4-C and 12-C, two d's), 39.68 (8-C,d), 36.74 (2'-C,t), 31.72 (9-C,d,), 29.139 (4',5' and 6'-C), 28.63 (8'-CO, 26.35 (N-Me,q), 26.00 (7'-C,d), 25.73 (3'-C), 20.84 (14-C,q), 19.23 (15-C,q) and 12.75 (17-C,q); umax (CHCl$_3$), 3400 (OH str.), 3300 (NH str.) 1690 (C=O str, ester), 1650 and 1540 (C=O amide I, and C=C), 1510 (amide II) cm$^{-1}$ λmax 222 nm (εm 10,700); m/e 513 (M$^+$), 495 ($-$H$_2$O), 269

227. (Found: M$^+$513.3297200; C$_{27}$H$_{47}$NO$_8$ requires M$^+$513.3301422).

EXAMPLE 2

Pseudomonic Acid Amide

Sodium pseudomonate (522 mg. 1mM) was dissolved in dry, distilled N,N-dimethylacetamide (10 ml) and the solution was cooled to $-15°$ C. iso-Butyl chloroformate (0.13 ml; p = 1.04; 1mM) was added and the temperature was maintained at $-15°$ C. for 10 minutes. A solution of 1% aqueous ammonia (2.0ml; >1mM) was added and the mixture was stirred for 1½ hours at room temperature. The mixture was diluted with water to approx. 75 ml., saturated with sodium chloride and extracted with ethyl acetate (4 × 15ml). The latter was washed with brine, aqueous sodium bicarbonate, dried over magnesium sulphate, filtered and the filtrate was evaporated to a slightly colored oil (269 mg). Thin layer chromatography in chloroform/methanol 9:1 revealed 1 major component at Rf 0.25 traces of impurities at 0.18 and 0.3. This material was applied to a 20 × 20 cm. 2mm thick preparative silica plate and eluted with 15% methanol in chloroform.

The band corresponding to the major compound was removed and eluted from the silica with 50. methanol in chloroform. After evaporation the product was obtained as a colourless oil (164 mg). Thin layer chromatography revealed 1 component in chloroform/methanol 9:1 at Rf 0.4 $\delta_H$(CDCl$_3$) 0.90 (3H,d,12-Me), 1.19 (3H,d,13-Me), 1.31 (methylene envelope), 2.19 (3H,s,vinylic Me), 2.70 (multiplets., exporide protons and 4-CH$_2$), 4.08 (2H,t,9'—CH), 5.76 (1H,s,vinylic $\underline{H}$) and 5.83 (2H, broad CON$\underline{H}_2$); umax (CHCl$_3$) 3450 (OH str.), 3350 (NH str.), 1700 (C=O ester), 1650-1670 (amide I, and C=C), 1600 (amide II)cm$^{-1}$; λmax 222nm (em 9,230); [α]$D^{20}$ - 5.02° (C,0.6 CHCl$_3$); m/e 499 (M$^+$, 481 (—H$_2$O), 255

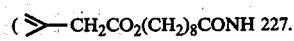 CH$_2$CO$_2$(CH$_2$)$_8$CONH 227.

(Found: M$^+$ 499.3137700; C$_{26}$H$_{45}$NO$_8$ requires M$^+$ 499.3144930).

EXAMPLE 3

Pseudomonic acid N,N-dimethylamide

Sodium pseudomonate (2.09g ; 4mM) was dissolved in dry, distilled N,N-dimethylacetamide (20ml) and cooled with stirring to −10° C. isoButyl chloroformate (0.53ml ; 4mM) was added maintaining the temperature at −10° C. for 10 minutes. A solution of dimethylamine in water (1M ; 4.2ml) was added and the solution stirred at 0° C. for half an hour at room temperature for 2 hours. The solution was evaporated to dryness in vacuo and the residue dissolved in ethyl acetate, which was washed with sodium bicarbonate solution, brine, dried over magnesium sulphate, filtered and evaporated in vacuo to an oil (1.197g). Thin layer chromatography and h.p.l.c. confirmed that the compound was homogeneous. The oil began to crystallise and on trituration with dry ether affording a white solid (776mg), mp 82°-85°. $\delta_H$ (CDCl$_3$) 5.70 (1H,s,vinylic $\underline{H}$), 4.03 (2H, t, 9'—$\underline{CH}_2$), 2.98 and 2.90 (two 3H,s,CON($\underline{CH}_3$)$_2$), 2.70 (multiplets, epoxide protons H$_{10}$ and H$_{11}$ 4-CH$_2$), 2.17 (3H,s,vinylic $\underline{CH}_3$), 1.31 (methylene envelope), 1.19 (3H,d, 13-$\underline{CH}_3$) and 0.91 (3H,s, 12-$\underline{CH}_3$);νmax (CHCl$_3$), 3450 (OH str.), 2950, 1710 (ester C=O) 1615 (broad, C=C and C=O amide)cm$^{-1}$ ;λmax (EtOH) 219 (em 14,700)nm; [α]$_D^{20}$ - 6.88° (c,1.0 CHCl$_3$); m/e 527 (M$^+$), 509 (—H$_2$O), 465 (509—N(CH$_3$)$_2$). (Found: M$^+$ 527.347132; C$_{28}$H$_{49}$NO$_8$ requires M$^+$ 527.347132).

Biological Data (a) Antibacterial activity against Gram-positive organisms

Table 1 shows the MIC values in (μg/ml) of the compounds of Examples 1 and 2 against six Gram-positive organisms:

Table 1

| | M.I.C. (μg/ml) | |
|---|---|---|
| | Compound of | |
| Organism | Example 1 | Example 2 |
| B. Subtilis | 0.25 | 0.25 |
| Staph. aureus Oxford | 0.5 | 0.5 |
| Staph. aureus Russell | 1.25 | 1.0 |
| Staph. aureus 1517 | 1.25 | 2.5 |
| Strep. faecalis | 125 | 100 |
| β-Haemolytic Strep. CN10 | — | 0.1 |

(b) Activity against N.gonorrhoeae

Table 2 shows M.I.C. values (μg/ml)* of the compounds of Examples 1 and 2 against twelve strains of N.gonorrhoeae compared to benzylpenicillin.

*Serial dilution in 10% horse blood agar. Incubated in a partial atmosphere of CO$_2$ for 24 hours at 37° C. Inoculated with one drop (0.001ml) of an overnight cell suspension.

Table 2

| | Benzyl | Compound of | |
|---|---|---|---|
| Strain | Penicillin | Example 1 | Example 2 |
| VDRL 67 | 0.05 | 0.002 | 0.002 |
| 69 | 0.1 | 0.002 | 0.002 |
| 70 | 0.1 | 0.005 | 0.005 |
| 72 | 0.2 | 0.01 | 0.01 |
| 77 | 0.1 | 0.005 | 0.02 |
| 82 | 0.5 | 0.05 | 0.05 |
| 87 | 0.01 | 0.01 | 0.005 |
| AR 229 | 1.0 | 0.05 | 0.05 |
| 2176 | 0.2 | 0.02 | 0.02 |
| H2057 | 0.005 | 0.005 | 0.005 |
| WHO VII | 0.005 | 0.005 | 0.002 |
| VD 79 | 0.2 | 0.02 | 0.02 |
| Oxford Staph. | 0.02 | 0.05 | 0.05 |

(c) Activity against mycoplasma

Table 3 shows the antimycoplasmal activities (in terms of M.I.C.) of the compounds of Examples 2 and 3 and demonstrates that both possess good antimycoplasmal activity in vitro against mycoplasmas from human and veterinary sources.

The method used to test for antimycoplasmal activity was as follows:

The minimal inhibitory concentration (MIC) of the pseudomonic acid amides was determined in Microtitre plates, by a modification of the metabolic-inhibition test (Taylor-Robinson, 1967). The compounds were serially diluted in sterile de-ionised water to give a range of concentrations from 250-0.5 μg/ml. Mycoplasma broth containing 1% (w/v) of glucose and 0.005% (w/v) of phenol red, was added at a strength to compensate for its dilution by the aqueous drug solution. Approximately 10$^4$ colony forming units of mycoplasma were added to each concentration of drug. Drug-free infected, non-infected and pH control wells were included on each plate. Plates were sealed with cellophane tape and incubated at 37° C. for 7 days. The MIC was the lowest concentration of compound that prevented a colour change in the mycoplasma broth caused by the metabolism of glucose by the mycoplasmas.

Reference

Taylor-Robinson, D., 1967. Mycoplasmas of various hosts and their antibiotic sensitivities. Post. Grad. Med. J., 43 Suppl. [March], 100.

TABLE 3

| | | | MIC μg/ml | | | | | |
|---|---|---|---|---|---|---|---|---|
| Source | Chicken | Mouse | | Cattle | | Pig | Man | |
| Compound | M. gallisepticum S6 | M. synoviae ATCC 25204 | M. pulmonis 'JB' | M. agalactiae ATCC 25025 | M. dispar H 225 | M. suipneumoniae (Laber) | M. pneumoniae 429 a | M. fermentans MWKL4 |
| Example 2 | <0.5 | <0.5 | <0.5 | <0.5 | <0.5 | <0.5 | 250 | <0.5 |
| Example 3 | <0.5 | <0.5 | <0.5 | <0.5 | <0.5 | 3.9 | 250 | <0.5 |

(d) Serum Binding

The degree of binding to human serum of the compounds of Examples 1 and 2 compared with that of pseudomonic acid was determined by the following procedure:

Test samples were mixed with human serum and placed in visking tubing. Serum binding was determined by ultrafiltration, the filtrate obtained being assayed by a hole-in-plate method using *Bacillus subtilis* ATCC 6633 against standards prepared in 0.05M pH7.0 phosphate buffer.

The results are shown in Table 4:

Table 4

| Compound | % unbound in human serum |
|---|---|
| Example 1 | 20 |
| Example 2 | 14 |
| Pseudomonic acid | |
| sample 1 | 6.6 |
| sample 2 | 6.8 |

What we claim is:

1. A compound of formula:

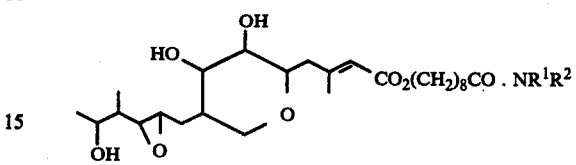

wherein $R^1$ and $R^2$ are the same or different and each is hydrogen or alkyl of 1 to 6 carbon atoms.

2. The compound according to claim 1 wherein $R^1$ is hydrogen and $R^2$ is methyl.

3. The compound according to claim 1 wherein each of $R^1$ and $R^2$ is hydrogen.

4. The compound according to claim 1 wherein each of $R^1$ and $R^2$ is methyl.

5. A compound of claim 1 in pharmaceutical dosage form with a pharmaceutically acceptable carrier, said compound being present in an amount effective to combat *Neisseria gonorrhoeae* upon oral, rectal or parenteral administration.

6. A pharmaceutical human or verterinary antibacterial composition comprising a compound of claim 1 in an effective antibacterial amount together with at least one conventional carrier or excipient.

7. A method for the treatment of human or veterinary bacterial infections which method comprises the administration to a patient or animal in need thereof an antibacterially effective amount of a compound of claim 1.

* * * * *